United States Patent [19]

Melet

[11] Patent Number: 5,054,498
[45] Date of Patent: Oct. 8, 1991

[54] DEVICE FOR TAKING SAMPLES OF BLOOD WITH FLOATING PISTON

[76] Inventor: Francois Melet, 9, chaussée Jules César, 95520 Osny, France

[21] Appl. No.: 399,544
[22] PCT Filed: Dec. 16, 1988
[86] PCT No.: PCT/FR88/00622
§ 371 Date: Aug. 16, 1989
§ 102(e) Date: Aug. 16, 1989
[87] PCT Pub. No.: WO89/05607
PCT Pub. Date: Jun. 29, 1989

[30] Foreign Application Priority Data

Dec. 17, 1987 [FR] France ................................ 87 17627

[51] Int. Cl.⁵ ............................................. A61B 5/00
[52] U.S. Cl. ........................................ 128/763; 128/770
[58] Field of Search ............... 128/760, 763, 765, 766, 128/770; 604/52, 190, 236–238, 249, 403, 405, 406

[56] References Cited

U.S. PATENT DOCUMENTS

| | | | |
|---|---|---|---|
| 3,920,002 | 11/1975 | Dye et al. | 128/760 |
| 4,215,702 | 8/1980 | Ayer | 128/766 |
| 4,361,155 | 11/1982 | Anastasio | 128/763 |
| 4,385,637 | 5/1983 | Akhavi | 128/763 |
| 4,492,634 | 1/1985 | Villa-Real | 128/763 |

FOREIGN PATENT DOCUMENTS 1242553 8/1960 France .
2176710 1/1987 United Kingdom .

*Primary Examiner*—Max Hindenburg
*Attorney, Agent, or Firm*—Browdy and Neimark

[57] ABSTRACT

A device for taking samples of arterial blood with a view to its subsequent gasometric analysis comprises a main body forming a reservoir in which a free piston travels. Said piston isolates the blood from the air and cannot be manipulated by the operator. The device also includes a filter located at the end of the piston stroke which is permeable to air and impermeable to blood, allows the operator to observe the blood as it advances, and acts as a barrier to excessive blood flow, and a stopper which ulitmately seals the system and facilitates its tranport. In contrast to conventional invasive systems, this device, which does not need to be sterilized, makes it possible to obtain a blood sample which, after sampling, is only minimally contaminated with the ambient air, is available in a sufficient quantity, and is only slightly coagulable.

12 Claims, 4 Drawing Sheets

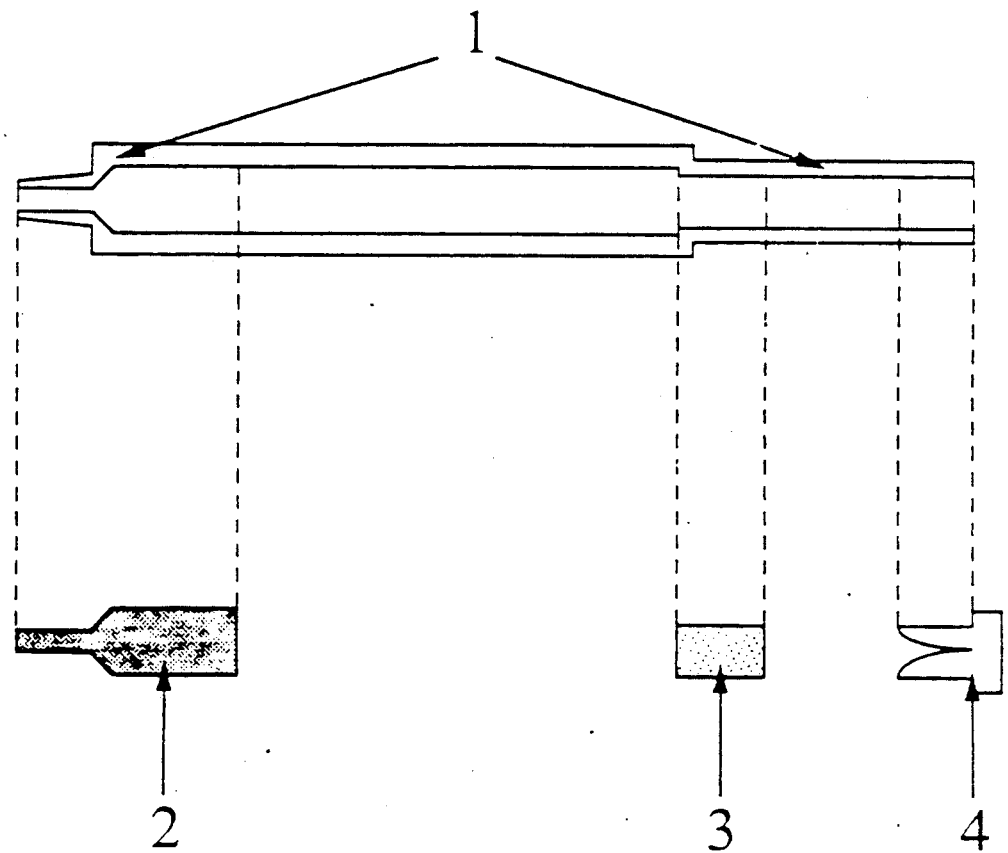
FIG_1

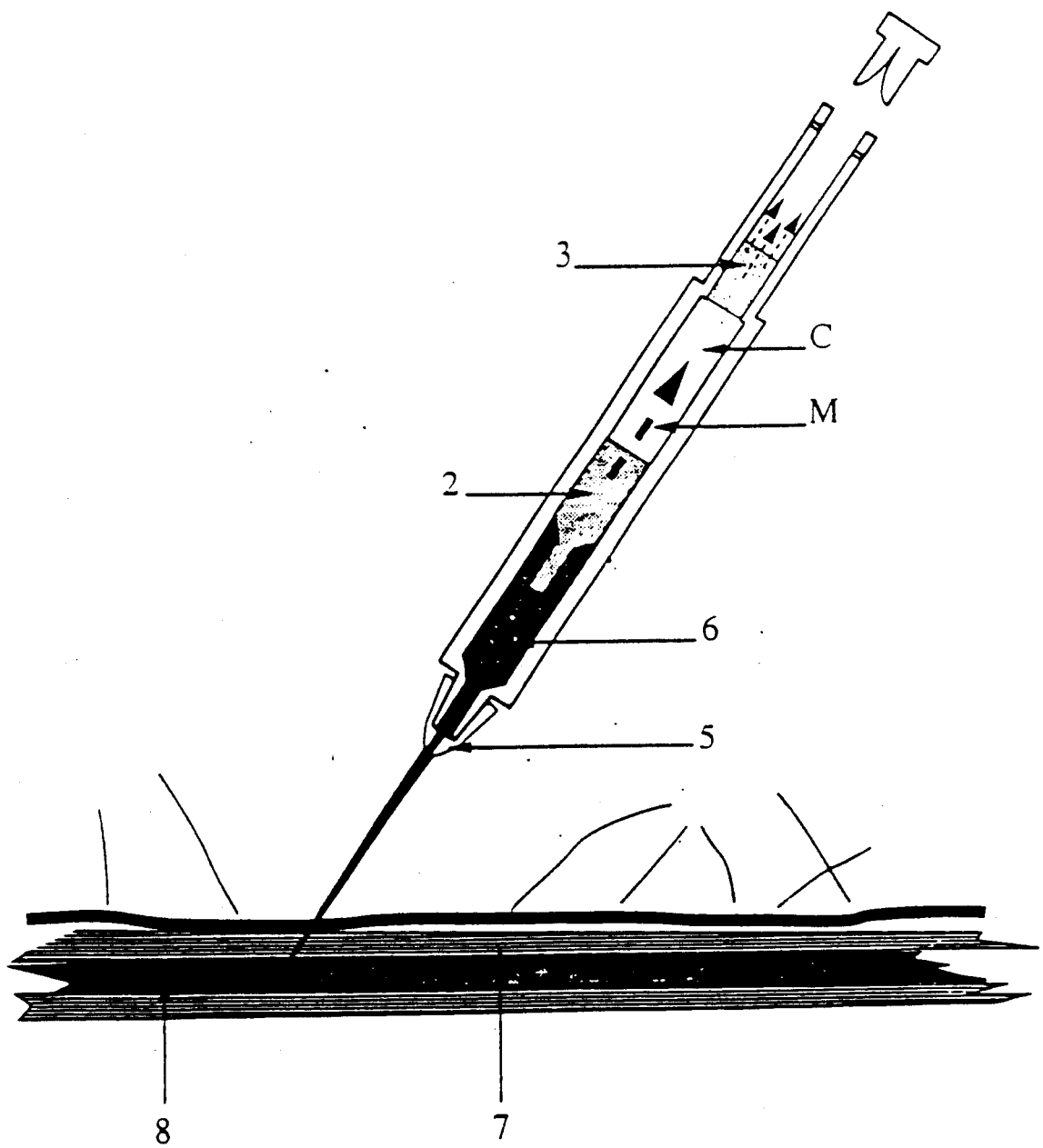
FIG_3

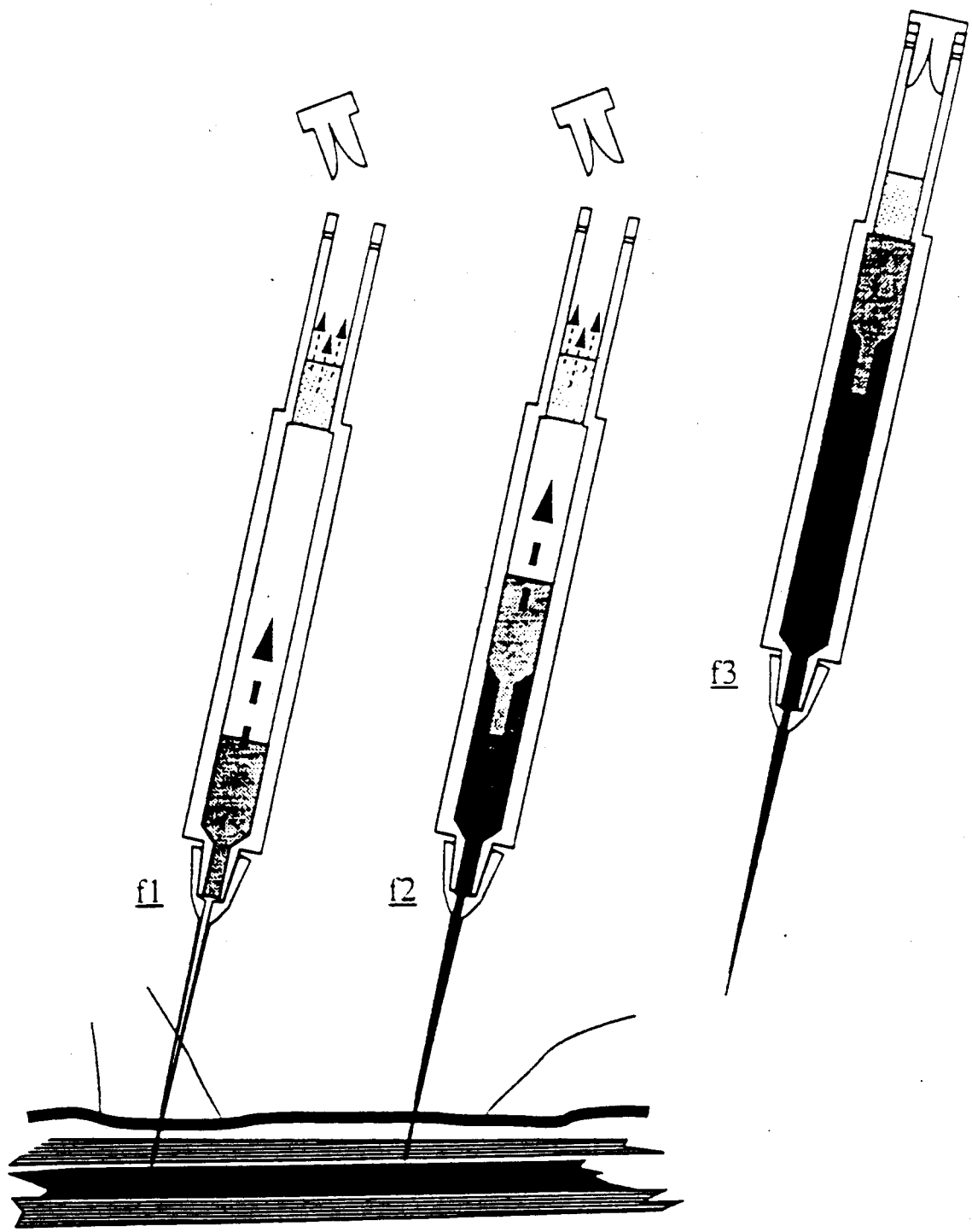
FIG_4

DEVICE FOR TAKING SAMPLES OF BLOOD WITH FLOATING PISTON

The present invention concerns a device for taking and storing blood for gasometric analysis. The present invention is more particularly concerned with a device which reduces contamination of the blood by ambient air, the stresses that can break down the internal gas equilibrium of the blood and the tendency of the blood to coagulate in situ.

DESCRIPTION OF PRIOR ART

Numerous prior art methods raise problems. These include methods which use the conventional form of syringe with a main body serving as a reservoir and a piston controlling the quantity sampled. This system, apart from the fact that it uses a large quantity of blood, has a large surface area of exchange with the air leading to contamination of the sampled blood. However, the major disadvantage of a system of this kind lies in the possibility, consequent upon the presence and function of the piston, of the operator reinjecting hazardous products such as the anticoagulating agents usually contained in the syringe.

Other prior art systems use a capillary device which makes it possible to collect a smaller quantity of blood. Also, the air/blood exchange surface area is reduced because of the small diameter of the capillary tube. However, these systems have the disadvantage of using glass capillary tubes which by their very nature activate coagulability of the blood (as a result of the 'glass-effect' phenomenon), are difficult to transport and store and sometimes sample too little blood to enable a number of analyses to be carried out afterwards.

SUMMARY OF THE INVENTION

The object of the invention is to overcome the defects and problems of the systems previously described. The sampling device in accordance with the invention is characterised in that it comprises an inert piston that is not accessible to the operator reducing gaseous exchange between the air and the blood and a blood-tight filter that is porous to air guaranteeing minimal contamination of the sample taken.

BRIEF DESCRIPTION OF THE DRAWINGS

FIG. 1 shows the present invention with its main elements. FIG. 3 shows the present invention in the artery of a patient. FIG. 4 shows the stages of using the present invention with collected blood.

DESCRIPTION OF THE PREFERRED EMBODIMENTS

Figures 2A, 2B:
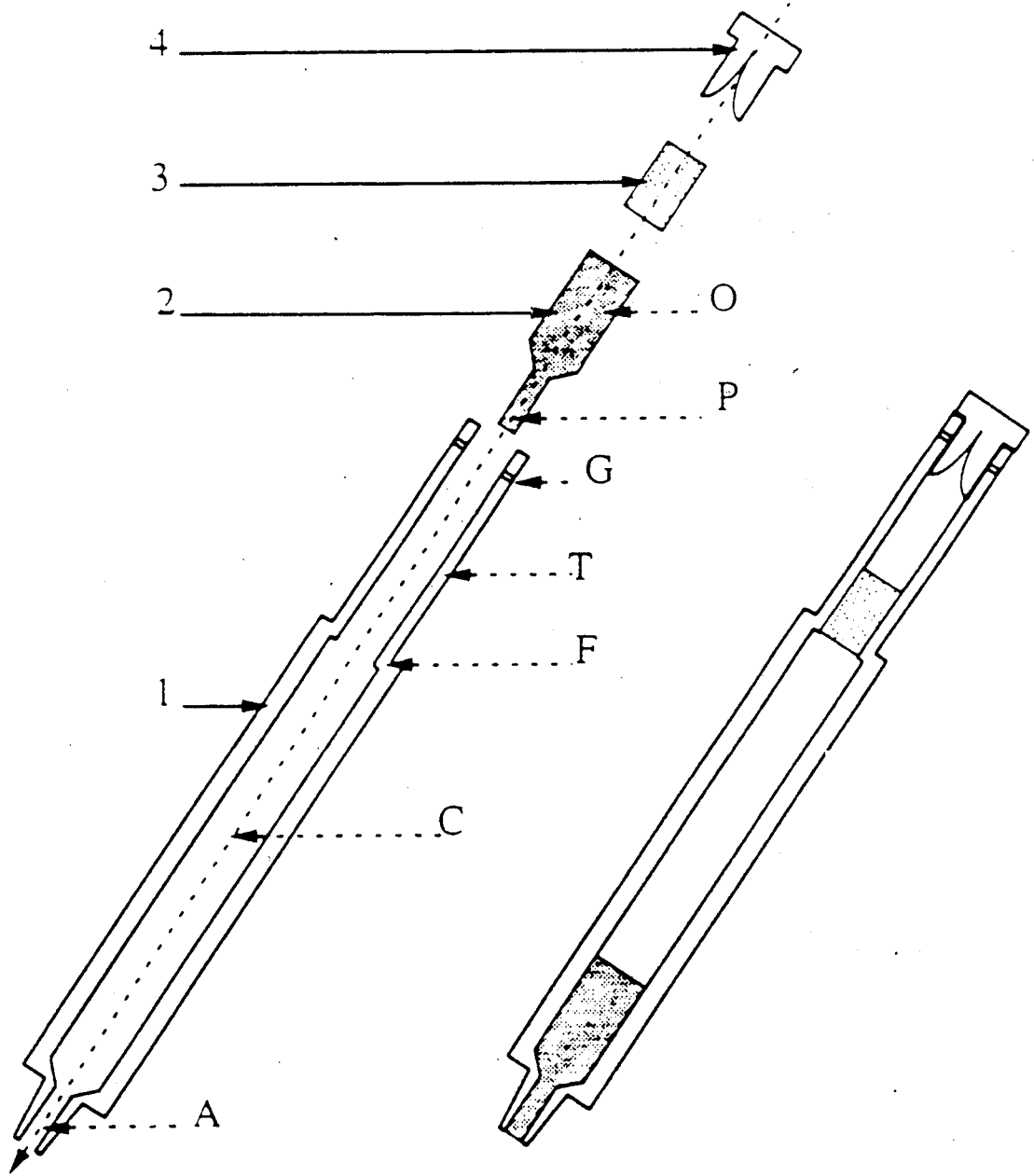
FIG. 2A shows the present invention with its main elements aligned to be placed together.
FIG. 2B shows the present invention with its elements in their initial places.

The system of the invention comprises a main body (1 FIG. 1) serving as a blood container, an inert cylindrical piston (2 FIG. 1), a blood-tight cylindrical plug porous to air (3 FIG. 1), and a plastics material plug (4 FIG. 1). In the following description of the invention the term anterior part (A FIG. 2) is arbitrarily applied to the part connecting to the sampling needle (5 FIG. 3) or the part in which the blood enters the system and the term posterior part (T FIG. 2) is arbitrarily applied to the opposite part of the system.

The main body (1) is formed of five characteristic parts. An anterior part (A) to which the sampling needle is connected, a central part (C) forming a chamber accommodating the piston and the collected blood, a narrower part (F) against which the piston abuts at the end of sampling, a posterior part (T) accommodating the filter (3) and a final part at the level of the hole (G FIG. 2) into which a plug may be fitted. The anterior part (A FIG. 2) is coaxial with the system and has an outside diameter enabling a sampling needle to be fitted and an inside diameter of at least 1.5 mm. This minimum inside diameter is necessary for the use of the invention with INSTRUMENTATION LABORATORY and RADIOMETER brand gasometric analysers, for example.

The inert piston (2) is formed of two characteristic parts: a main part and an anterior part (P) coaxial to the main part (0 FIG. 2). The anterior part (P FIG. 2) of the piston (2) has a smaller diameter than its main part (O) which is also slightly smaller than the inside diameter of the anterior part (A) of the main body (1). Before sampling this cylindrical part (P) mates with the shape of the anterior part (A FIG. 2) of the main body (1), so reducing the dead volume at the orifice of the sampling system. The advantage of this male/female type assembly (FIG. 2) is to reduce air/blood contact, so reducing contamination of the blood as it enters the system. This device is fundamental in the implementation of the invention.

The porous filter (3) at the level of the abutment (F FIG. 2) in the posterior part (T) of the main body (1) has the property of allowing air to pass and remaining blood-tight. It enables the air compressed in the chamber (C FIG. 2) of the main body (1) to escape until the piston (2) abuts against the thinner part (F FIG. 2) of the main body (1), so functioning as a regulator during the entry of the blood sample. This filter also creates a barrier reducing the surface area for gaseous exchange between the blood contained in the central part (C) and ambient air situated in the central part (C) and ambient air situated in the posterior part (T) of the main body (1). The size and porosity of this filter are adapted to suit the arterial pressure of the blood sample. It is necessary for blood to enter the system at a speed which is neither too high nor too low, enabling the user to view the filling of the system with blood. This could require different lengths of the posterior chamber (T) of the main body (1).

The plug (4) is fitted at the end of the posterior part (T) of the main body (1). A hole (G) in the posterior part (T) of the main body (1) enables the posterior part to be depressurised when the plug (4) is fitted. The hole (G) will be obstructed at the end of the travel of the plug (4). The plug makes it possible to reduce the volume of air in the posterior chamber (T) of the main body (1) to limit contamination of the blood by the air over time. The length of the posterior part (T) of the main body (1) and that of the filter (3) are adjusted to enable the plug (4) to be fitted in such a way that when fitted it is positioned against the filter (3). It also enables easy transportation of the system from the sampling site to the analysis site without the blood being able to escape from the anterior part (A) of the main body (1) in the vertical position.

Use of the system entails a number of phases: a first phase of fitting a sterile needle (5 FIG. 3) to the anterior part (A) of the main body (1), a second phase (f1 FIG. 4) in which the needle penetrates the body of the patient (7 FIG. 3) as far as the artery from which the blood is to be sampled (8 FIG. 3), a third phase (f2 FIG. 4) in which the blood rises into the sampling system, the arterial pressure pushing (M FIG. 3) the piston (2) back to the abutment (F), a fourth phase (f3 FIG. 4) in which the needle is removed, and finally a final phase (f3 FIG. 4) of fitting the plug (4) and a conventional system for protecting the needle.

The invention has the fundamental advantage of offering no possibility of reinjection into the patient of the content of the chamber (C) of the main body (1). This advantage is decisive in the manufacturing cost of the system since the latter has no need to be sterile, which also circumvents the administrative constraints relating to the sale of syringes. Finally, the main body (1) and the piston (2) are manufactured from a non-wettable polypropylene type material which does not initiate coagulation of the sampled blood. This material is also translucent, which enables the entry of blood into the system to be viewed.

The system in accordance with the invention will be used as a capillary sampling means with the various gasometric analysers available on the market, in other words the blood will be aspirated by the analyser to perform measurements on the sample.

I claim:

1. A device for sampling arterial blood for gasometric analysis comprising:
   a main body (1) defining a chamber functioning as a blood reservoir with an anterior section (A) having an orifice, a central section (C), and a posterior section (T),
   a piston (2) positioned inside the central section of said main body and having a first part (O) of complementary cross-section to said central section so as to be freely movable only in response to an increased or reduced pressure at the orifice of said anterior section (A), said piston comprising a second part (P) concentric to said first part, said second part being shaped and positioned to mate with the interior of said anterior section so as to minimize the residual air volume in said anterior section before sampling the arterial blood,
   a piston stop (F) at a posterior end of the central section (C) of the main body formed by an anterior end of the posterior section (T) of the main body,
   a pressure regulator and blood contamination barrier means comprising a blood-tight filter (3) porous to air positioned inside the posterior section (T) of the main body, posterior to said piston stop (F), and
   a transportation facilitator and supplementary air barrier means comprising a removable plug (4) positioned inside a posterior end of the posterior section (T) of the main body.

2. A device according to claim 1 wherein said piston (2) is positioned inside the main body so that said piston is inaccessible to the operator and freely movable towards the posterior section of said main body only by arterial blood pressure and towards the anterior section of said main body only by aspiration force.

3. A device according to claim 1 wherein the anterior section (A) of said main body is shaped for fitting into a sampling needle.

4. A device according to claim 3 wherein the anterior section (A) of said main body has an interior diameter of at least 1.5 mm.

5. A device according to claim 3 wherein said piston first part (O) has a diameter slightly smaller than that of the internal diameter of the central section of the main chamber and said second part (P) of the piston has a diameter slightly smaller than the anterior section of the main body so that said piston minimizes the residual air volume in the anterior section of the main body.

6. A device according to claim 1 wherein said piston (2) is comprised of a material having a density less than that of blood and means whereby, when said piston is subjected to a thrust force (M) due to the arterial pressure, causes said piston to advance into the central part of the main body as the blood enters and remain in a raised position after sampling.

7. A device according to claim 1 wherein said piston (2) is shaped for advancing into the central section (C) of the main body as blood enters the main body and for stopping at the piston stop (F), said piston stop being set relative to the main body such that the blood sample in the main body is of a predetermined volume.

8. A device according to claim 1 wherein said blood-tight filter (3) is positioned at the anterior end of the posterior section (T) of the main body in line with the piston stop (F) preventing diffusion of the blood into the narrow part of the main body after sampling.

9. A device according to claim 1 wherein said plug (4) is positioned inside the posterior end of the posterior section (T) of the main body reducing the volume of residual air in said part.

10. A device according to claim 1 where in said main body is shaped so that the length of the posterior section (T) of the main body enables the plug (4) to be positioned against the blood-tight filter (3) when said plug is inserted.

11. A device according to claim 1 further comprising a hole (G) positioned in the posterior end of the posterior section (T) of the main body whereby said posterior section is depressurized when the plug (4) is inserted.

12. A device according to claim 1 wherein said main body (1) and said piston (2) are comprised of a non-wettable polypropylene type material.

* * * * *